United States Patent

Soeda et al.

[11] Patent Number: 5,907,031
[45] Date of Patent: May 25, 1999

[54] MILK WHEY PROTEIN-CONTAINING POWDER AND PROCESS FOOD OBTAINED BY USING THE SAME

[75] Inventors: Takahiko Soeda; Katsutoshi Yamazaki; Hiroyuki Tanno; Chiho Kuhara, all of Kawasaki, Japan

[73] Assignee: Ajinomoto Co., Inc., Tokyo, Japan

[21] Appl. No.: 08/904,846

[22] Filed: Aug. 1, 1997

[30] Foreign Application Priority Data

Aug. 1, 1996 [JP] Japan ..................... 8-233523

[51] Int. Cl.$^6$ .............. C07K 1/00; A23C 9/12; A23C 21/00
[52] U.S. Cl. .............. 530/350; 426/41; 426/42; 426/583; 426/656
[58] Field of Search .................. 426/34, 41, 42, 426/43, 583, 656; 530/366, 350

[56] References Cited

U.S. PATENT DOCUMENTS

| | | | |
|---|---|---|---|
| 4,917,904 | 4/1990 | Wakameda et al. | 426/7 |
| 5,055,310 | 10/1991 | Nonaka et al. | 435/68.1 |
| 5,082,672 | 1/1992 | Hamad et al. | 426/7 |
| 5,093,028 | 3/1992 | Kyogoku et al. | 252/315.1 |
| 5,156,956 | 10/1992 | Motoki et al. | 435/193 |
| 5,330,778 | 7/1994 | Stark et al. | 426/531 |
| 5,416,196 | 5/1995 | Kitabake et al. | 530/366 |
| 5,420,025 | 5/1995 | Takagi et al. | 435/193 |
| 5,514,573 | 5/1996 | Yasueda et al. | 426/63 |
| 5,518,742 | 5/1996 | Soeda et al. | 435/193 |
| 5,607,849 | 3/1997 | Yasueda et al. | 435/193 |
| 5,658,605 | 8/1997 | Soeda et al. | 426/7 |
| 5,670,192 | 9/1997 | Budofsen et al. | 423/34 |
| 5,681,598 | 10/1997 | Kuraishi et al. | 426/36 |
| 5,707,668 | 1/1998 | Anderson | 426/42 |
| 5,731,183 | 3/1998 | Kobayashi etal. | 435/193 |
| 5,736,356 | 4/1998 | Sano et al. | 435/68.1 |
| 5,750,498 | 5/1998 | Soeda et al. | 512/4 |

FOREIGN PATENT DOCUMENTS

| | | |
|---|---|---|
| 93-19610 | 10/1993 | WIPO . |
| 93-22930 | 11/1993 | WIPO . |
| 94-21130 | 9/1994 | WIPO . |

*Primary Examiner*—Nina Bhat
*Attorney, Agent, or Firm*—Oblon, Spivak, McClelland, Maier & Neustadt, P.C.

[57] ABSTRACT

A process is described in which a solution of milk whey protein is reacted with a transglutaminase, heated, and then dried. The resulting milk whey protein composition, and food products containing the resulting milk whey protein composition are also described. The milk whey protein composition has an excellent taste and imparts a smooth and pleasant feel on the palate.

17 Claims, No Drawings

MILK WHEY PROTEIN-CONTAINING POWDER AND PROCESS FOOD OBTAINED BY USING THE SAME

BACKGROUND OF THE INVENTION

1. Field of the Invention

The present invention relates to a milk whey protein-containing powder obtained by reacting a solution containing a milk whey protein with transglutaminase, heating the reaction solution at a high temperature, then drying the resulting product. The invention also relates to an animal meat paste food, a fish meat paste food and emulsified foods obtained by using the milk-whey protein-containing powder.

2. Discussion of the Background

Milk whey protein is found in whey, a by-product from the production of cheese or casein from milk or a skim milk powder. In countries where cheese and so forth are produced, attempts have been made to recover milk whey protein and use it as a food material with the aim of environmental conservation and to more effectively use natural resources.

The production of milk whey protein concentrate via ultrafiltration has been reported in which the protein content of the concentrate is between approximately 50 and 70%. Further, a separate whey protein having a protein content of approximately 90% or more has been produced to improve the gelation, emulsifying capacity and foaming capacity of the protein.

Meanwhile, in recent years, studies on milk whey protein-containing products having lower protein content (approximately 30%) than that of conventional products as a food material have been actively conducted at a global level in order to effectively utilize the active ingredients of whey, such as protein, sugar, mineral and the like in the diet with a minimum of whey processing.

When the milk whey protein-containing product discharged as a by-product is used in various foods, the foods have a rough feel as well as a bad taste upon passage through the throat owing to the milk whey protein, and is therefore undesirable. The rough feeling and the bad taste upon passage through the throat do not apply to the overall milk protein. This is because these problems do not apply to caseins that are a main component of a milk protein.

To solve the problems of the rough feeling and the bad feeling upon passage through the throat which are found in the milk whey protein, a technique to lower the molecular weight of this protein using an enzyme has been generally employed. However, when the molecular weight of a protein using an enzyme, the desired gelation properties of the milk whey protein are decreased.

Accordingly, a milk whey protein-containing powder (1) which retains the desirable characteristic properties of milk whey protein, such as gelation, emulsifying capacity and the like and (2) which is excellent in throat feel and taste upon eating has been in demand. To cope with such problems, the following attempts have been already made.

The retention of gelatinization ability and the decrease in number of bacteria have been attempted by bringing a non-denatured whey protein powder in contact with super-heated steam of 110 to 130° C. for 10 to 20 seconds (refer to Japanese Patent Publication No. 108, 191/1995). This method is effective for retaining the gelatinization ability and decreasing the number of bacteria. However, the problems such as the rough feeling and the bad taste upon passage through the throat which are caused by the heating even for a short period of time still remain.

A technique has also been studied in which protein particles having an average particle diameter of from approximately 40 to 50 $\mu$m are prepared by partially denaturing a milk whey protein (degree of denaturation between 55 and 80%), and added to foods such as mayonnaise, salad sauce, ice cream and the like (U.S. Pat. No. 5,494,696). However, the above-described problems relating to the rough feeling and the bad taste upon passage through the throat have not completely been eliminated.

Accordingly, the above-mentioned problem of providing a milk whey protein-containing powder that both (1) retains the desirable characteristic properties of milk whey protein, such as gelation, emulsifying capacity, and the like, and (2) is excellent in throat feel and taste has not yet been realized.

Other researchers, Shin-Ya Tanimoto and John E. Kinsel (J. Agric. Food Chem., 1988, 36, 281–285) have reported the thermal stability of a polymer mixture obtained by treating $\beta$-lactoglobulin with transglutaminase at 99° C. or less and the effect on protein solubility. Their experiments revealed that the insolubilization of a protein is inhibited. However, the properties of the thus-treated protein, for example, gelation, water holding capacity, emulsifying and foaming capacity, were not examined at all. Moreover, feeling upon eating, such as a feeling upon passage through the throat or the like, has not been referred to at all. Further, this report has described experimental results in a pure system of $\beta$-lactoglobulin which is a only minor component of milk protein. However, there is nothing in this report to suggest the treatment of the overall milk whey protein-containing product that contains various substances other than B-lactoglobulin.

In a modified milk protein-containing material (Japanese Laid-Open (Kokai) No. 160,957/1991) and a pickle for processed edible meat (Japanese Laid-Open (Kokai) No. 255,426/1995), a milk protein is reacted with a transglutaminase. Casein, a major component of a milk protein, is imagined as this milk protein. However, these documents do not suggest the elimination of the problems of the milk whey protein solved by the present invention, such as the rough throat feel that nevertheless do not apply to casein.

SUMMARY OF THE INVENTION

It is an object of the present invention to provide a milk whey protein-containing powder that both (1) retains the desirable characteristic properties of milk whey protein, such as gelation, emulsifying capacity, and the like, and (2) has an excellent throat feel and taste upon eating.

Accordingly, the first embodiment of the present invention relates to a composition that includes:

a milk whey protein containing $\epsilon$-($\lambda$-Glu)Lys crosslinks.

The second embodiment of the present invention relates to a composition that includes:

the reaction products of a reaction mixture that includes:

a milk whey protein; and a transglutaminase.

The third embodiment of the present invention relates to a process that includes:

heating a solution containing:

(i) a milk whey protein; and (ii) a transglutaminase to a temperature of 100–140° C.

Another embodiment of the present invention relates to a food product that includes the the milk whey protein composition.

The present inventors have conducted studies to solve the above-mentioned problems, and have consequently found that a product obtained by reacting a solution containing a milk whey protein composition with transglutaminase and heating the reaction gives an excellent feeling on the palate, yet retains the desirable properties of milk whey protein such as gelation, emulsifying capacity, and the like.

DESCRIPTION OF THE PREFERRED EMBODIMENTS

Other features of the invention will become apparent in the course of the following descriptions of exemplary embodiments which are given for illustration of the invention and are not intended to be limiting thereof.

The present invention provides a milk whey protein containing powder (1) which has characteristic properties of a milk whey protein, such as gelation, emulsifying capacity and the like and (2) which is excellent in throat feel and taste. The milk whey protein, upon treatment with transglutaminase, can exhibit an increased molecular weight and a densified protein network structure due to intermolecular or intramolecular $\epsilon$-($\lambda$-Glu)Lys crosslinking.

The solution of the milk whey protein-containing composition in the present invention preferably contains a milk whey protein that can be obtained as a by-product in the production of cheese, casein or the like from milk, skim milk, or skim milk powder as a starting material. Preferably, such a milk whey includes lactose and a protein as solid contents. Preferably, the solution includes approximately 94% of water, approximately 1% of a protein, approximately 4.5% of sugar, approximately 0.5% of ash, and a trace amount of fat and the like. Preferably, a concentrate obtained by concentrating components such as a protein and the like approximately 2 to 5 times through ultrafiltration, and a milk whey protein-containing solution formed by adding water to a commercially available milk whey protein-containing powder having a protein content of 30% or more is included in the solution of the milk whey protein-containing composition in the present invention.

The solution of the milk whey protein containing composition having a protein content of 10% or less is preferable in view of controlling the interaction between protein molecules in heat sterilization, more preferably 5% or less. These ranges include all values and subranges therebetween.

Preferably, the transglutaminase includes a calcium-independent one and a calcium-dependent one. An example of the former is a transglutaminase derived from microorganisms (Japanese Laid-Open (Kokai) No. 27,471/1989), the entire contents of which are incorporated by reference. Examples of the latter are transglutaminase derived from the guinea pig liver (refer to Japanese Patent Publication (Koukoke) No. 50,382/1989), the entire contents of which are hereby incorporated by reference, transglutaminase derived from animal blood (also called Factor XIII), and transglutaminase derived from fish ("Journal of Japan Fisheries Academy", by Seki Nobuo et al., vol, 56, No. 1, pp. 125–132 (1990), the entire contents of which are hereby incorporated by reference. Further, a transglutaminase produced through gene recombination (Japanese Laid-Open (Kokai) Nos. 300,889/1989, 199,883/1993 and 225,775/1994), the entire contents of which are hereby incorporated by reference, is also available. Thus, any of these transglutaminases can be used, and the origin thereof and the method of producing the same are not particularly limited.

In view of both performance and economics, the calcium-independent transglutaminase is preferable. For example, the transglutaminase derived from microorganisms (Japanese Laid-Open (Kokai) No. 27,471/1989) satisfies all of the above-mentioned conditions, and it is considered most preferable.

The preferred method of obtaining a desired milk whey protein-containing powder by reacting a solution containing a milk whey protein with transglutaminase is described below.

First, a solution of a milk whey protein-containing composition is mixed with a transglutaminase. Preferably, the amount of the transglutaminase is between 0.2 and 200 units, more preferably between 1 and 100 units, most preferably between 5 and 50 units per gram of protein in the solution of the milk whey protein-containing composition. These ranges include all values and subranges therebetween. When the amount of the transglutaminase is less than 0.2 units, the cohesiveness given through the heating is the same as that provided without the addition of the transglutaminase, and the throat feel is not improved. When it is more than 200 units, the effect provided by the addition of the transglutaminase is the same as that in the above-mentioned range, and it is economically disadvantageous.

Preferably, the solution containing the transglutaminase is maintained under conditions that ensure the enzyme activity of the transglutaminase. Accordingly, the reaction temperature is preferably between approximately 0 and 60° C., and the reaction time is preferably between approximately 5 minutes and 48 hours. The reaction is more preferably conducted at a temperature of approximately 20 to 50° C. for approximately 30 minutes to 2 hours. When the reaction is conducted at quite a low temperature for quite a short period of time, the enzyme activity is not exhibited. When it is conducted at quite a high temperature for quite a long period of time, the transglutaminase is deactivated.

The solution containing the milk whey protein composition resulting from the reaction with the transglutaminase is then heated, preferably at 100 to 140° C., more preferably 110 to 130° C. and most preferably 120 to 125° C., for 1 to 120 seconds, more preferably 10 to 100 seconds, and most preferably 40 to 60 seconds, for sterilization and deactivation of the enzyme. These ranges include all values and subranges therebetween. When the temperature is too high and the time is too long, the protein may be thermally denatured. This heating is preferably UHT, and the treatment is conducted at a high temperature for a short period of time. The UHT may be indirect heating by which steam is passed through a plate or direct heating by which steam is fed directly into the protein solution.

The heat-treated solution of the milk whey protein composition is then dried. Spray drying is preferred. In order to control the thermal denaturation of the protein as much as possible, it is preferred to maintain the exhaust temperature in the dryer at 80° C. or less, more preferably, 60° C. or less, and most preferably, 40° C. or less. These ranges include all values and subranges therebetween.

The above-mentioned steps make it possible to prepare the milk whey protein-containing powder of the present invention more practically in view of the number of bacteria or the properties of the protein.

The thus-obtained milk whey protein-containing powder can be utilized in various processed foods requiring gelation, emulsifying capacity, and foaming capacity, for example, fish meat paste products such as a boiled fish paste product, animal meat paste products such as sausage, milk products such as ice cream and yogurt, and emulsified foods such as mayonnaise and dressing.

The amount of the milk whey protein-containing powder to be added to the processed food is not particularly limited. The weight ratio thereof to the processed food is between approximately 0.03 and 10%, preferably between approximately 1 and 5%. The thus-obtained processed food has a smooth feeling upon eating without a rough feeling.

The activity unit of the transglutaminase referred to in the present invention is measured and defined as follows. The reaction is preferably conducted using benzyloxycarbonyl-IFO 13819) in a predetermined amount shown in Table 1 was added to a solution of a milk whey protein obtained by dissolving 100 parts of a milk whey protein concentrate powder (made by DOMO, Netherlands, protein content approximately 35% by weight) in 900 parts of water, and the mixed solution was gently stirred. The pH of the solution was 6.6. Subsequently, this solution was maintained at 50° C. for 30 minutes, and then at 120° C. for 10 seconds by blowing high temperature steam using an ejector-like mixing tube to conduct heating.

The thus-heat-treated solution was injected into a cyclone which had been retained under reduced pressure of 600 mmHg, and rapidly cooled to 60° C. The resulting product was spray-dried at approximately 80° C. (exhaust gas temperature in the dryer). In this manner, seven types of the milk whey protein-containing powders shown in Table 1 were obtained.

The above-mentioned treatment was also conducted except that the transglutaminase was not added, and the resulting product was used as a control.

These products were subjected to an organoleptic evaluation by expert panelists. The results are also shown in Table 1.

TABLE 1

| Amount of TG (units/g · protein) | Hardness (score) | Smoothness (score) | Water holding capacity (%) | Comments |
|---|---|---|---|---|
| 0 (control) | 5 | 5 | 78.0 | rough, brittle, bad upon passage through the throat |
| 0.5 | 5.6 | 5.5 | 82.2 | slightly smooth, slightly good upon passage through the throat |
| 1 | 6.6 | 6.4 | 85.0 | smooth, good upon passage through the throat |
| 5 | 7.3 | 7.1 | 87.4 | very smooth, very good upon passage through the throat |
| 10 | 7.7 | 7.9 | 90.1 | very smooth, very good upon passage through the throat |
| 30 | 8.5 | 8.1 | 93.2 | very smooth, very good upon passage though the throat |
| 50 | 9.1 | 8.3 | 93.6 | smooth, very good upon passage through the throat |
| 100 | 7.3 | 6.1 | 84.4 | smooth, good upon passage through the throat |

TG: transglutaminase

L-glutamylglycine and hydroxylamine as substrates. Hydroxamic acid, when formed, is converted to an iron complex in the presence of trichloroacetic acid. Then, the absorbance of the reaction system is measured at 525 nm. The amount of hydroxamic acid formed is measured using a calibration curve, and the activity is calculated (Japanese Laid-open Kokai) Nos. 27,471/1989 and 27,471/1989), the entire contents of which are incorporated by reference.

Having generally described this invention, a further understanding can be obtained by reference to certain specific examples which are provided herein for purposes of illustration only and are not intended to be limiting unless otherwise specified.

EXAMPLES

Example 1

A transglutaminase (specific activity 1 unit/mg) derived from an actinomycetous microorganism belonging to the genus Streptoverticillium (*Streptoverticillium mobaraense*

As shown in Table 1, the gel of the milk whey protein containing powder prepared by the addition of the transglutaminase was excellent organoleptically (hardness and smoothness) and physically (water holding capacity) in comparison with the transglutaminase-free (control) product.

The gelability of the milk whey protein-containing powder was evaluated as follows.

(1) Method of preparing a gel:

Thirty grams of water were added to 40 g of the milk whey protein-containing powder, and the mixture was kneaded for 15 minutes using a kneader. This mire was packed into a casing tube (folding width 47 mm). Then, the resulting product was heated in hot water at 90° C. for 40 minutes, and cooled to room temperature with city water to prepare a gel for evaluation.

(2) Evaluation:

The score to evaluate "Hardness" and "Smoothness" in Table 1 is an average of values given by five panelists using a 10-point method in which the control product is given 5 points. Further, the comments are average ones of the five panelists.

"Water holding capacity" was measured using a moisture meter (physicochemical tester manufactured by K. K. Yoshida Seisakusho). That is, a gel having a weight of approximately 4 g was held between two filter papers, and a load of 2 kg was exerted thereon for 60 seconds. Then, the water content remaining in the gel was measured from the amount of water absorbed in the filter papers. The water holding capacity was expressed in terms of a ratio (%) of this water content relative to the original water content of the gel. The higher the ratio, the higher the water holding capacity.

Example 2

To a milk whey concentrate (protein content approximately 2%) that was obtained by concentrating milk whey that was discharged in the production of casein through the usual ultrafiltration method were added 5 units, per gram of the protein in the concentrate, of the same transglutaminase (specific activity 1 unit/mg) as that used in Example 1, and the mixture was gently stirred. This mixture was maintained at 25° C. for 60 minutes, and then subjected to indirect steam heating of a UHT plate system at 110° C. for 60 seconds. Subsequently, the thus-heat treated concentrate was subjected to the same procedure as that given in Example 1 to obtain a milk whey protein-containing powder (invention product).

The above-mentioned treatment was also conducted except that the transglutaminase was not added to prepare a milk whey protein-containing powder (control).

Thirty grams of water were added to 40 g of each of the two types of milk whey protein-containing powders disclosed above. The mixture was packed into a casing tube, and heated at 90° C. for 40 minutes. The resulting heated gel was subjected to the organoleptic evaluation. Consequently, the invention product containing the transglutaminase was quite smooth and had an excellent feeling upon passage through the throat in comparison with the control gel.

Example 3

Water (1,500 parts) was added to 100 parts of a separate milk whey protein (made by Nissei Kyoeki K. K., protein content approximately 85% by weight) to obtain a solution of a milk whey protein. To this solution was added 10 units, per gram of the protein of this solution, of the same transglutaminase (specific activity 1 unit/mg) as that used in Example 1, and the mixture was gently stirred. The pH of the solution was 6.6. The solution was neutralized to a pH of 7.0 with sodium hydroxide, and then maintained at 50° C. for 30 minutes. Subsequently, the same procedure as in Example 1 was conducted to obtain a milk whey protein containing powder (invention product).

Additionally, a milk whey protein-containing powder (control) was prepared as above except that a transglutaminase was not added.

To each of the above-mentioned milk whey protein-containing powders was added water in an amount two times (by weight) as large as the amount of the powder. The mixture was packed into a casing tube, and then heated at 90° C. for 40 minutes to obtain a heated gel. In the organoleptic evaluation, the gel of the present invention in comparison with the control gel was very smooth, had an excellent feeling upon passage through the throat, and was rich in viscosity.

In the following Examples 4 to 7, various processed foods were produced using the product treated with 10 units, per grams of the protein, of the transglutaminase (TG) as described in Example 1 (milk whey protein-containing powder of the present invention) as well as the TG-free product (TG-free milk whey protein-containing powder (control)) for comparison.

Example 4

Boiled fish paste:

Ground meat of a frozen walleye pollack ("SA-grade Ground Meat" made by Maruha K. K.) was flaked in frozen state. Thirty grams of sodium chloride and 600 g of ice water were added to 1,000 g of flaked meat, and these were mixed well using a Stefan cutter. Subsequently, to the mixture were added 50 g of wheat starch ("Esusan Ginrei" made by Ajinomoto Co., Inc.), 50 g of sugar, 20 g of mirin (sweet sake), 10 g of a seasoning powder and 30 g of the product treated with 10 units of TG per gram of the protein as described in Example 1. These were mixed using a Stefan cutter such that the temperature of the final product reached 8° C. The thus-obtained paste was packed into a casing tube, warmed at 30° C. for 60 minutes, then heated at 90° C. for 30 minutes, and cooled to prepare a boiled fish paste casing (invention product).

For comparison, a boiled fish paste (control) was prepared in the above-mentioned manner except that 30 g of the product not treated with TG was used instead of 30 g of the product treated with 10 units of TG per gram of the protein.

The two boiled fish pastes described above were subjected to the organoleptic evaluation, and the results are shown in Table 2 below. As is clear from Table 2, the boiled fish paste (control) containing the product not treated with TG was less elastic, and had a dry feeling upon eating and upon passage through the throat. In contrast, the boiled fish paste (invention product) containing the product treated with 10 units of TG per gram of the protein had a stickiness peculiar to a boiled fish paste, and was smooth and pleasant upon passage through the throat, having a feeling upon eating inherent in a boiled fish paste.

Mechanical tests for a gel strength and a strain were also conducted, and the results are shown in Table 2. In this table, "Gel strength" and "strain" were measured as follows.

(1) Gel strength:

The gel was cut round to a thickness of 30 mm, and a gel strength (g) of the cut piece was measured from a pattern according to a breaking test using a rheometer of Fudo Kogyo K. K. At this time, a ball having a diameter of 7 mm was used as a plunger. The higher the gel strength value (g), the harder the gel.

(2) Strain:

A distance in which the plunger was penetrated through the gel until the gel was broken was measured from the above-mentioned pattern according to the breaking test, and indicated as a strain (mm). The larger the strain value, the more flexible the gel.

| Sample | Gel strength (g) | Strain (mm) | Organoleptic evaluation |
|---|---|---|---|
| Invention | 556 | 13.5 | good feeling upon passage through the throat without roughness |
| Control | 487 | 9.7 | inappropriate as a fish meat paste with notable roughness |

Example 5

Sausage:

Thirty grams of sodium chloride and 400 g of ice water were added to 1,000 g of pork lean meat and 400 g of pork fat, and these were mixed well using a Stefan cutter. To the mixture was added 50 g of starch ("Esusan Ginrei" made by Ajinomoto Co., Inc.), 10 g of a seasoning powder and 30 g of the product treated with 10 units of TG per gram of the protein as described in Example 1. These were mixed using a Stefan cutter such that the temperature of the final product reached 10° C. The thus-obtained meat paste was packed into an edible casing tube, then dried in a smoking chamber at 60° C. for 30 minutes, smoked at the same temperature for 15 minutes, and finally boiled with steam at 80° C. for 40 minutes to prepare a sausage (invention product).

For comparison, a sausage (control) was prepared in the above-mentioned manner except that 30 g of the product not treated with TG were used instead of 30 g of the product treated with 10 units of TG per gram of the protein as described in Example 1.

The two types of the sausages were subjected to the organoleptic evaluation. Consequently, the sausage (control) not treated with TG was less elastic, and had a dry feeling upon eating and upon passage through the throat. Meanwhile, the sausage (invention product) containing the product treated with 10 units of TG per gram of the protein was so elastic as to give a satisfactory feeling upon biting, was smooth and had a good feeling upon passage through the throat. Thus, it had a feeling upon eating peculiar to a pork sausage.

Example 6

Mayonnaise:

A solution obtained by dissolving 5 g of the product treated with 10 units of TG per gram of the protein as described in Example 1 in 40 g of water was mixed with 20 g of the yolk. Then, 375 g of salad oil, 50 g of vinegar and 10 g of sodium chloride were further added thereto. The emulsification was conducted using a domestic hand mixer to prepare mayonnaise (invention product).

For comparison, mayonnaise (control) was prepared in the above-described manner except that 5 g of the product not treated with TG was used instead of 5 g of the product treated with 10 units of TG per gram of the protein as described in Example 1.

The two types of mayonnaise were subjected to the organoleptic evaluation. Consequently, the mayonnaise (control) not treated with TG had a rough feeling upon eating, and quite a bad feeling upon passage through the throat. Meanwhile, the mayonnaise treated with 10 units of TG per gram of the protein was smooth, and had a good feeling upon passage through the throat. It had a feeling upon eating inherent in mayonnaise.

Example 7

Dressing:

The product (3.5 g) treated with 10 units of TG per gram of the protein as described in Example 1 was added to 3 g of water, and the resulting solution was mixed with 14 g of the yolk, 0.75 g of xanthane gum and 0.75 g of guar gum. To this mixed solution were added 205 g of water, 62 g of sugar and 3.5 g of sodium chloride, and these were uniformly mixed. To this aqueous mixed solution was further added 375 g of salad oil, 50 g of vinegar and 10 g of sodium chloride. The emulsification was conducted using a domestic hand mixer to prepare dressing (invention product).

For comparison, dressing (control) was prepared in the above-described manner except that 3.5 g of the product not treated with TG was used instead of 3.5 g of the product treated with 10 units of TG per gram of the protein as described in Example 1.

The two types of the dressing were subjected to the organoleptic evaluation. Consequently, the dressing (control) not treated with TG had a rough feeling upon eating or an unpleasant strongly acid taste. Meanwhile, the dressing (invention product) treated with 10 units of TG per gram of the protein was smooth, and had a good feeling upon passage through the throat as well as a mild taste. Thus, it had a feeling upon eating and a taste inherent in dressing.

Processed foods prepared by using the milk whey protein-containing powder as a starting material, such as a sausage, a boiled fish paste, dressing and the like, have a smooth feeling on the palate and a good taste.

This application is based on Japanese Patent Application 8-233523, filed Aug. 1, 1996, the entire contents of which are hereby incorporated by reference.

What is claimed as new and desired to be secured by Letters Patent of the United States is:

1. A milk whey protein comprising $\epsilon$-($\lambda$-Glu)Lys crosslinks which is separated from whole milk.

2. The milk whey protein of claim 1, wherein said crosslinks are intermolecular or intramolecular crosslinks.

3. The milk whey protein of claim 1, which is in the form of a powder.

4. A food product containing a food and the crosslinked milk whey protein of claim 1.

5. The food product of claim 4, wherein said food is selected from the group consisting of fish meat paste, animal meat paste, milk products and emulsifed foods.

6. The food product of claim 5, wherein said food is selected from the group consisting of boiled fish paste, sausage, ice cream, yogurt, mayonnaise and dressing.

7. A milk whey protein comprising $\epsilon$-($\lambda$-Glu)Lys crosslinks which is separated from whole milk, wherein said crosslinked milk whey protein is obtained by a process comprising:

contacting a solution comprising (i) a milk whey protein separated from whole milk and (ii) a transglutaminase, to form said crosslinks, heating the solution containing the milk whey protein comprising $\epsilon$-($\lambda$-Glu)Lys crosslinks at a temperature of 100 to 140° C., and then drying the solution to obtain the milk whey protein comprising $\epsilon$-($\lambda$-Glu)Lys crosslinks in the form of a powder.

8. The crosslinked milk whey protein of claim 7, wherein said contacting step is conducted between approximately 0 and 60° C.

9. A food product containing a food and the crosslinked milk whey protein of claim 7.

10. The food product of claim 9, wherein said food is selected from the group consisting of fish meat paste, animal meat paste, milk products and emulsifed foods.

11. The food product of claim 10, wherein said food is selected from the group consisting of boiled fish paste, sausage, ice cream, yogurt, mayonnaise and dressing.

12. A method of making a milk whey protein comprising $\epsilon$-($\lambda$-Glu)Lys crosslinks separated from whole milk, comprising:

contacting a solution comprising (i) a milk whey protein separated from whole milk and (ii) a transglutaminase, to form said crosslinks, heating the solution containing the milk whey protein comprising $\epsilon$-($\lambda$-Glu)Lys crosslinks at a temperature of 100 to 140° C., and then drying the solution to obtain the milk whey protein comprising ε-(λ-Glu)Lys crosslinks in the form of a powder.

13. The method of claim 12, wherein said contacting step is conducted between approximately 0 and 60° C.

14. The method of claim 12, wherein said transglutaminase is present in an amount of 0.2–200 units per gram of said milk whey protein.

15. The method of claim 12, wherein said transglutaminase is derived from a source selected from the group consisting of actinomycetous microorganisms, guinea pig liver, animal blood, and fish.

16. The method of claim 12, wherein said transglutaminase is a calcium-independent transglutaminase.

17. The method of claim 12, further comprising drying said solution to obtain said isolated and purified milk whey protein in powder form.

* * * * *

UNITED STATES PATENT AND TRADEMARK OFFICE
CERTIFICATE OF CORRECTION

PATENT NO. : 5,907,031
DATED : May 25, 1999
INVENTOR(S) : Takahiko Soeda, et al.

It is certified that error appears in the above-identified patent and that said Letters Patent is hereby corrected as shown below:

On the title page, item [56] insert the following:

FOREIGN PATENT OR PUBLISHED FOREIGN PATENT APPLICATION

|   |   | DOCUMENT NUMBER |   |   |   |   |   |   | PUBLICATION DATE | COUNTRY OR PATENT OFFICE | CLASS | SUBCLASS | TRANSLATION YES | NO |
|---|---|---|---|---|---|---|---|---|---|---|---|---|---|---|
|   | JP | 0 | 3 | 1 | 6 | 0 | 9 | 5 7 | 07/10/91 | Japan(Abstract Only) |   |   |   |   |
|   | WO | 94/ | 2 | 1 | 1 | 3 | 3 |   | 09/29/94 | WIPO |   |   |   |   |
|   | JP | 0 | 2 | 0 | 4 | 2 | 9 | 4 3 | 02/13/90 | Japan(Abstract Only) |   |   |   |   |

OTHER REFERENCES (Including Author, Title, Date, Pertinent Pages, etc.)

SHIN-YA TANIMOTO, J. E. KINSELLA: "ENZYMATIC MODIFICATION OF PROTEINS: EFFECTS OF TRANSGLUTAMINASE CROSS-LINKING ON SOME PHYSICAL PROPERTIES OF BETA-LACTOGLOBULIN" JOURNAL OF AGRICULTURAL AND FOOD CHEMISTRY, VOL. 36, - 1988 PAGE 281-285 XP002088327

DATABASE WPI SECTION CH, WEEK 9629, DERWENT PUBLICATIONS LTD., LONDON, GB; CLASS D12, AN 96-280726, XP002088328 & JP 08 116924 A (SNOW BRAND MILK PROD CO LTD), MAY 14, 1996 (ABSTRACT ONLY)

DATABASE WPI, SECTION CH, WEEK 9444, DERWENT PUBLICATIONS LTD., LONDON, GB; CLASS D12, AN 94-353652, XP002088329 & JP 06 276954 A (SAKAI m), OCTOBER 4, 1994 (ABSTRACT ONLY)

Signed and Sealed this

Twenty-first Day of December, 1999

Attest:

Q. TODD DICKINSON

*Attesting Officer*     *Acting Commissioner of Patents and Trademarks*